United States Patent [19]

Hirose

[11] Patent Number: 4,716,245

[45] Date of Patent: Dec. 29, 1987

[54] PROCESS FOR PRODUCING 2,6-NAPHTHALENEDICARBOXYLIC ACID

[75] Inventor: Isao Hirose, Matsuyama, Japan

[73] Assignee: Teijin Petrochemical Industries, Ltd., Tokyo, Japan

[21] Appl. No.: 853,693

[22] Filed: Apr. 18, 1986

[30] Foreign Application Priority Data

Apr. 24, 1985 [JP] Japan ................................ 60-86563
Nov. 19, 1985 [JP] Japan ............................... 60-257800

[51] Int. Cl.$^4$ .......................................... C07C 51/265
[52] U.S. Cl. .................................. 562/416; 562/417; 562/421; 562/488
[58] Field of Search ............... 562/416, 417, 421, 488

[56] References Cited

U.S. PATENT DOCUMENTS 3,846,487 11/1974 Shigeyasu et al. ................ 562/416
3,856,855 12/1974 Yamashito et al. ............... 562/416
3,870,754 3/1975 Yamashito et al. ............... 562/416

FOREIGN PATENT DOCUMENTS 49-25936 7/1974 Japan ................................ 562/416

Primary Examiner—Werren B. Lone
Assistant Examiner—Vera C. Clarke
Attorney, Agent, or Firm—Sherman and Shalloway

[57] ABSTRACT

A process for producing 2,6-naphthalenedicarboxylic acid which comprises oxidizing 2,6-diisopropylnaphthalene or its oxidation derivative with molecular oxygen in a reaction medium containing at least 70% by weight of an aliphatic monocarboxylic acid selected from actic acid, propionic acid and a mixture of these in the presence of an oxidation catalyst comprising (A) at least one compound of a heavy metal element selected from cobalt and manganese and (B) bromine or a bromine compound; characterized in that said oxidation is carried out in the presence of 1.1 to 15 gram-atoms, per gram-atom of bromine, of an alkali metal.

17 Claims, No Drawings

PROCESS FOR PRODUCING 2,6-NAPHTHALENEDICARBOXYLIC ACID

This invention relates to an improved process for producing 2,6-naphthalenedicarboxylic acid by oxidizing 2,6-diisopropylnaphthalene or its oxidation derivative with molecular oxygen. More specifically, it relates to a process for producing 2,6-naphthalenedicarboxylic acid in a very high yield by performing the oxidation in a solvent containing at least one compound of a particular aliphatic monocarboxylic acid in the presence of a catalyst containing a heavy metal or a bromine compound and bromine element.

2,6-Naphthalenedicarboxylic acid (to be sometimes abbreviated "2,6-NDA" hereinafter) or its derivatives such as an ester or an acid chloride is a compound valuable as a dibasic acid component of various polyesters and polyamides. Particularly, poly(ethylene 2,6-naphthalate) prepared from 2,6-NDA and ethylene glycol has better heat resistance and mechanical properties than polyethylene terephthalate, and is useful as a polymer giving films or textile products.

A conventional process for producing 2,6-NDA comprises the oxidation reaction of 2,6-dimethylnaphthalene, for example, oxidizing 2,6-dimethylnaphthalene with molecular oxygen in an acetic acid solvent in the presence of a catalyst composed of a cobalt element, manganese element and bromine element. According to this process, the oxidation of 2,6-dimethylnaphthalene to 2,6-NDA is relatively easy, and the desired 2,6-NDA of a relatively high purity can be obtained in a high yield.

The method of producing the starting 2,6-dimethylnaphthalene in this process, however, is complex, and this compound of high purity or quality is difficult to obtain in quantities at low costs. Known methods for producing 2,6-dimethylnaphthalene include, for example, methylation of naphthalene, isomerization of dimethylnaphthalene, disproportionation of monomethylnaphthalene, and transalkylation. All of these methods are not free from the formation of isomers other than 2,6-dimethylnaphthalene, particularly 2,7-dimethylnaphthalene, and the isolation of 2,6-dimethylnaphthalene from the mixed dimethylnaphthalenes is extremely difficult because 2,6-dimethylnaphthalene and 2,7-dimethylnaphthalene have very close melting and boiling points and very similar dissolving characteristics.

2,6-NDA obtained by the oxidation of 2,6-dimethylnaphthalene containing 2,7-dimethylnaphthalene gives a polymer such as polyethylene naphthalate having lower heat resistance or mechanical properties than a polymer obtained from highly pure 2,6-NDA.

In contrast, diisopropylnaphthalene can be easily synthesized by alkylation (isopropylation) of naphthalene with propylene. This alkylation reaction is very easy, and the resulting alkylation product, as required, can be easily disproportionated, isomerized or transalkylated to give a reaction product having a high 2,6-diisopropylnaphthalene content. The separation of 2,6-diisopropylnaphthalene from the resulting reaction product is also easy.

Investigations of the present inventor, however, have shown that when 2,6-diisopropylnaphthalene (to be sometimes abbreviated "2,6-DIPN" hereinafter) is oxidized under known reaction conditions suitable for the oxidation of p-xylene or 2,6-dimethylnaphthalene, the yield of 2,6NDA is extremely low, usually 50% or less and since large amounts of by-products are formed, the purity of the resulting 2,6-NDA is low. For this reason, it has been found impossible to obtain 2,6-NDA from 2,6-DIPN industrially by employing known reaction conditions for oxidizing p-xylene or 2,6-dimethylnaphthalene. Accordingly, there has been no industrial interest in the production of 2,6-NDA from 2,6-DIPN as a starting material.

No clear reason has been assigned to the unsatisfactory results of the oxidation of 2,6-DIPN under known reaction conditions. The present inventor presumes, however, from many experiments he has so far conducted that in the oxidation of 2,6-DIPN having an isopropyl group and a naphthalene ring which has high activity and low oxidation stability, radicals and hydroperoxide form very easily and rapidly as a result of hydrogen extraction of the isopropyl group in the early stage of the reaction; in the meanwhile, bromine in the catalyst adds to the isopropyl radicals to reduce the activity of the catalyst; consequently, the cleavage of the naphthalene ring is promoted and the catalyst is rapidly inactivated owing to the formation of a stable complex (e.g., an ortho-benzene carboxylic acid complex, etc.); and that because these reactions proceed successively, the desired oxidation does not sufficiently proceed and rather side-reactions are promoted.

The present inventor and his co-workers previously found a method in which the aforesaid side reactions in the oxidation of 2,6-DIPN or its oxidation derivative are inhibited by using a much larger amount of cobalt and/or manganese than heretofore been known for the starting material, and thus 2,6-NDA is obtained in a high yield (see EP-A-No. 142719). This method is very useful in industrial practice since high purity 2,6-NDA can be obtained in a higher yield than in any previously known methods. It, however, has the defect that because large amounts of catalyst metals which are expensive and detrimental to the environment are used, much consideration should be given to the operation of handling these metals during the reaction, their recovery and recycling, pollution control, etc.

This prompted the present inventor to continued investigations for an industrially more advantageous method of oxidizing 2,6-DIPN or its oxidation derivative. As a result, it has now been found that 2,6-NDA can be obtained in a very high yield by causing an alkali metal to be present in the reaction system in an excessive amount with respect to bromine used as a catalyst.

According to this invention, there is provided a process for producing 2,6-naphthalenedicarboxylic acid which comprises oxidizing 2,6-diisopropylnaphthalene or its oxidation derivative with molecular oxygen in a reaction medium containing at least 70% by weight of an aliphatic monocarboxylic acid selected from acetic acid, propionic acid and a mixture of these in the presence of an oxidation catalyst comprising (A) at least one heavy metal element selected from cobalt and manganese and (B) a bromine element; characterized in that said oxidation is carried out in the presence of 1.1 to 15 gram-atoms, per gram-atom of the bromine element, of an alkali metal.

It has generally been known that in a method of oxidizing an alkyl-substituted aromatic hydrocarbon, particularly p-xylene, with molecular oxygen in an aliphatic monocarboxylic acid using a catalyst comprising a heavy metal such as cobalt and/or manganese and bromine, the reaction is carried out in the presence of an alkali component, for example, an alkali metal such as sodium or potassium, an alkaline earth metal such as calcium, or ammonium. In this method, a bromide such as NaBr, KBr, CaBr$_2$ or NH$_4$Br or a hydroxide such as NaOH or KOH is used as a common source of bromine and the alkali component in combination with HBr, CoBr$_2$, MnBr$_2$ or the like.

To the best of the knowledge of the present inventor, the effect of adding such an alkali metal or the like to the reaction system is very small on the essence of the reaction. For example, Example 10 and Comparative Examples 7 to 9 of U.S. Pat. No. 3,846,487 show that the yield of terephthalic acid obtained by oxidizing p-xylene using cobalt acetate, manganese acetate and hydrobromic acid as a catalyst is much the same as that of terephthalic acid obtained by repeating the above reaction using sodium bromide, potassium bromide or ammonium bromide instead of hydrobromic acid.

Japanese patent publication No. 8252/1984 shows that p-xylene is oxidized similarly in the presence of a specific amount of an alkali metal atom with respect to bromine (the alkali metal/Br atomic ratio=not more than 7/9). The patent document, however, fails to refer to the change of the yield of terephthalic acid, and shows only a change in the properties of the product.

U S. Pat. No. 3,870,754 shows an example of oxidizing dimethyl naphthalene in the presence of an ammonium salt added (Examples 1 to 3) and in the absence of it (Example 19). But there is hardly any difference in the yield of the resulting naphthalenecarboxylic acid, and its yield in these examples is in the range of 94 to 96 mole%.

The prior patent documents have many example of adding alkali metals in such an oxidation reaction, but fail to give a description of a marked effect on the yield of the oxidation product. Rather, some describe that the presence of alkali metals is deleterious on the properties of the oxidation product (for example, British Pat. No. 1,511,181 and Japanese patent publication No. 25936/1974). From these descriptions of the prior art, it is understood that the addition of alkali metals does not bring about any essential improvement on the oxidation reaction of an alkyl-substituted hydrocarbon with molecular oxygen in an aliphatic monocarboxylic acid in the presence of a heavy metal and bromine, and it is rather anticipated that the alkali metals will exert a deleterious effect on the yield of the final oxidation product.

In fact, experiments conducted by the present inventor have shown that in the oxidation of p-xylene or dimethylnaphthalene under conventional conditions, the addition of an alkali metal or ammonium did not bring about even a 5% increase in yield, and in many cases, the yields remained the same or rather decreased.

In view of the disclosure of the prior art, it is surprising and unexpected to those skilled in the art that when 2,6-DIPN or its oxidation derivative is oxidized in the presence of a specific amount of an alkali metal, 2,6-NDA is obtained in a very high yield as shown in Examples given hereinbelow.

The starting material used in the process of this invention is 2,6-diisopropylnaphthalene (2,6-DIPN) or its oxidation derivative or a mixture of these. Preferably, the starting material is of a high purity, but needs not to be pure. It may contain other components of the types and amounts which do not adversely affect the oxidation reaction or the purity and coloration of the resulting 2,6-NDA.

The oxidation derivative of 2,6-DIPN is formed by the oxidation of 2,6-DIPN either separately or in situ and finally gives the desired 2,6-NDA. Preferably, the starting material of this invention is represented by the following general formula (I).

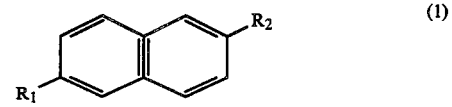

wherein R$_1$ is a group selected from the class consisting of

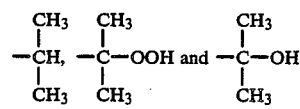

and R$_2$ is a group selected from the class consisting of the same groups as those described for R$_1$ above,

—COOH and —CHO and may be the same as or different from R$_1$.

Preferred starting materials are those of formula (I) in which R$_1$ and R$_2$ are identical or different and selected from

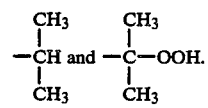

The oxidation catalyst used in this invention comprises (A) at least one compound of a heavy metal element selected from the group consisting of compounds of cobalt, compounds of manganese and mixtures thereof (to be referred to as component A), and (B) bromine or a bromine compound (to be referred to as component B).

Components A and B may be in any form capable of being dissolved in the oxidation reaction system in accordance with this invention. Components A and B are usually in the form of a simple substance or a compound.

Examples of cobalt and manganese compounds forming component A include their oxides; their hydroxides, their inorganic salts such as carbonates or halides, especially bromides; and their organic carboxylic acid salts such as formic acid, acetic acid, propionic acid, naphthenic acid or aromatic carboxylic acids, especially NDA. The bromides and the aliphatic carboxylic acid salts, particularly the acetates are preferred.

Bromine-forming component B may be in the form of any organic or inorganic compound which dissolves in the oxidation reaction system to generate a Br ion. Specific examples include molecular bromine (Br$_2$), inorganic bromine compounds such as hydrogen bromide and hydrobromides, and organic bromine compounds, for example alkyl bromides such as methyl bromide, ethyl bromide, bromoform and ethylene bromide, and brominated fatty acids such as bromoacetic acid and polybromoacetic acid. Preferred among them are molecular bromine, hydrogen bromide, sodium bromide, potassium bromide, lithium bromide, ammonium bromide, ethyl bromide, bromoacetic acid, cobalt bromide and manganese bromide.

It is generally believed that in these oxidation catalysts, component B as a simple or complex salt ion is coordinated with or bonded to component A or forms a counter ion with respect to component A, and as such, the oxidation catalysts participate in the reaction. Accordingly, the use of a metal element or insoluble metal compound which is difficult of forming such an ion during the reaction, or an organic bromine compound which is difficult of liberating a bromine ion upon decomposition at the reaction temperatures, such as a nuclearly brominated aromatic compound, as an oxidation catalyst produces only a small effect and is not advantageous.

Bromine added to the oxidation reaction system in the reaction of this invention, in whatever compound form it may be given, tends to add partly to the isopropyl side-chain of 2,6-DIPN or its oxidation derivative either directly or secondarily and form a side chain organic bromine compound thereof. This compound more or less liberates a bromine ion under the oxidation reaction conditions in accordance with this invention. Accordingly, the side-chain bromine compounds of 2,6-DIPN or its oxidation derivative are also effective as a source of component B of the catalyst used in the process of this invention.

The amount of the oxidation catalyst is not strictly restricted, and may be varied depending upon the types of the starting material and the solvent, the reaction conditions, etc. However, as the present inventors describe in the above-cited EP-A-No. 142719, as far as the reaction yield in the oxidation reaction in accordance with this invention is considered, better results are obtained when the proportion of component A based on the starting material and its concentration in the solvent are higher, and it is virtually difficult to set an upper limit to them.

However, industrially, the use of an excessive amount of the catalyst reduces productivity. Furthermore, the use of the specified amount of an alkali metal in the present invention makes it possible to achieve a high reaction yield by using a much smaller amount of the catalyst than is described in the above-cited patent. The amount of component A in industrial practice may be generally 0.0035 to 0.1 gram-atom, preferably 0.007 to 0.07 gram-atom, more preferably 0.008 to 0.05 gram-atom, as the total amount of the heavy metals per 100 g of the aliphatic monocarboxylic acid solvent.

Component A may be cobalt or manganese alone or a mixture of both, preferably the latter. The preferred mixing ratio of cobalt and magnanese in the mixture depends upon the reaction temperature, the reaction time, the amount of the catalyst used, the amount of the solvent used, etc. Usually, the preferred Co:Mn atomic ratio is from 1:99 to 99:1, particularly from 5:95 to 60:40.

The present inventor has observed that the optimum concentration of bromine used as component B of the catalyst used in the reaction depends not only on the concentration of component A, but also other reaction conditions involving the reaction temperature, the concentration of the starting materials and the amount of the solvent. It is difficult therefore to determine definitely the concentration of bromine used in the process of this invention. Generally, the concentration of bromine is conveniently such that the atomic ratio of component A as metal to bromine is from 1:0.1 to 1:20, preferably from 1:0.3 to 1:10, more preferably from 1:0.5 to 1:5.0. Generally, this ratio may be higher as the amount of component A is smaller.

One great characteristic of the process of this invention is that the oxidation reaction is carried out in the presence of an excessive amount of an alkali metal. Generally, the alkali metal is introduced into the reaction system in the form of an inorganic salt such as a hydroxide, carbonate or bromide, or an organic acid salt such as an acetate or propionate. Examples of suitable alkali metals are potassium, sodium and lithium. Potassium and sodium are preferred, and potassium is especially preferred.

The optimum concentration of the alkali metal that can be present in the reaction system in accordance with this invention cannot always be determined definitely because it depends upon the type of the alkali metal used and other reaction conditions. However, it is at least 1.1 gram-atoms per gram-atom of bromine present in the reaction system. If it is below this limit, no substantial increase in the yield of 2,6-NDA can be expected. If, however, the concentration of the alkali metal based on bromine is too high, the yield of 2,6-NDA may rather decreases depending upon the ratio of bromine to the alkali metal. From a practical viewpoint, the use of too much alkali metal is ineffective, and deleterious in many cases. From this standpoint, the upper limit of the amount of the alkali metal used is desirably 15 g -atoms/gram-atom of bromine.

The amount of the alkali metal used is therefore 1.1 to 15 gram-atoms, preferably 1.3 to 8 gram-atoms, more preferably 1.5 to 6 gram-atoms, per gram-atom of bromine present in the reaction system. Generally, the concentration of the alkali metal in the aliphatic monocarboxylic acid solvent is conveniently not more than 0.4 g-atom, preferably not more than 0.25 gram-atom, per 100 g of the aliphatic monocarboxylic acid used.

The reaction medium used in the process of this invention contains at least 70% by weight, preferably at least 80% by weight, of acetic acid, propionic acid, or a mixture of both. The remainder of the reaction medium is not particularly restricted so long as it does not substantially exert an adverse effect on the oxidation reaction in accordance with this invention. For example, the remainder may be water or another aliphatic monocarboxylic acid such as n-butyric acid. The use of a solvent in which the weight ration of acetic acid to propionic acid is generally from 0:100 to 75:25, preferably from 20:80 to 70:30, more preferably from 33:67 to 67:33 is advantageous in yield and economy.

Investigations of the present inventor have shown that the use of propionic acid as the reaction medium brings about some excellent advantages over the case of using acetic acid. One advantage is that the yield of the desired 2,6-NDA increases. Specifically, when the oxidation is carried out in the same catalyst concentration, the yield of 2,6-NDA increases markedly, and the concentration of the catalyst to be used to achieve the same yield of 2,6-NDA can be decreased markedly. A second advantage is that in propionic acid, 2,6-NDA has less coloration than in acetic acid, and the subsequent purification operation becomes easier.

Intrinsically, the reaction medium is used to dissolve the starting material and the catalyst at least partly and to facilitate contact of them with molecular oxygen. In addition, it promotes or facilitates the dispersion of heat, the removal of heat, the flowing of the reaction mixture, the crystal growth of the reaction product, etc., and thus makes it easy to practice the process of this invention industrially.

The amount of the reaction medium should therefore be determined according to the purpose for which it is used, and is not essentialy restricted. In practice, the amount of the reaction medium is at least 1 times, preferably 2 to 10 times the total weight of the starting material (2,6-DIPN), its oxidation intermediate and the desired 2,6-NDA in the reaction system.

If the amount of the reaction medium is too small, the objects of the present invention are not fully achieved, and smooth proceeding of the reaction is hampered. Even if the reaction medium is used in a larger amount than that described above, the reaction itself is not promoted, but rather losses of the reaction medium by oxidation and combustion increase to disadvantage.

The process of this invention is performed by oxidizing 2,6-DIPN or its oxidation derivative with molecular oxygen in the reaction medium in the presence of the oxidation catalyst.

The proportion of the starting 2,6-DIPN or its oxidation derivative to be used to the reaction system is conveniently such that its concentration in the reaction system based on the oxidation catalyst is maintained at 2 moles or less, preferably 1 mole or less, especially advantageously 0.5 mole or less, per gram atom of the component A (the total of heavy metal elements) of the oxidation catalyst.

When the process of this invention is carried out continuously or semi-continuously, the disappearance of the starting material by the reaction is generally rapid so long as the reaction temperature and the concentration of oxygen (partial pressure of oxygen) are maintained within preferred conditions. It is comparatively easy therefore to maintain the concentration of the starting material during the reaction at not more than 2 moles.

Advantageously, the reaction medium is used in such a proportion that the total concentration of the heavy metal elements (component A) of the oxidation catalyst in the reaction is 0.0035 to 0.1 gram-atom, preferably 0.007 to 0.07 gram-atom, more preferably 0.008 to 0.05 gram-atom, per 100 gram of the aliphatic monocarboxylic acid solvent used.

Pure oxygen or a gaseous mixture of it with a diluting inert gas may be used as a source of molecular oxygen used in the process of this invention. For practical purposes, air is the most easily obtainable gas containing molecular oxygen. Air may be used as such or if required, concentrated or diluted with oxygen or an inert gas.

The oxidation reaction in the process of this invention can be carried out under normal atmospheric pressure, but is accelerated under elevated pressures.

Generally, the reaction proceeds more rapidly as the partial pressure of oxygen in the reaction system is higher. From a practical standpoint, the sufficient partial pressure of oxygen is at least 0.1 kg/cm$^2$-abs., preferably at least 0.2 kg/cm$^2$-abs., for example about 0.1 to 8 kg/cm$^2$-abs. Even when the total pressure of a gaseous mixture of oxygen with an inert gas is not more than 30 kg/cm$^2$-G, the reaction rapidly proceeds to give 2,6-NDA in a high yield.

The reaction proceeds even at 60° C. But since at this time, the rate of the reaction is slow, it is not entirely economical. If the reaction temperature exceeds 240° C., the proportion of by-products increases to decrease the yield of 2,6-NDA. Furthermore, at high temperatures, losses of the solvent such as acetic acid and propionic acid by combustion cannot be ignored. Generally, the reaction temperature that can be advantageously used in the process of this invention is preferably 120° to 240° C., more preferably 160° to 230° C., especially preferably 180° to 220° C.

In performing the oxidation reaction of the process of this invention, the oxidation catalyst, the reaction medium and the starting material are fed into a reactor (as required, after heating) simultaneously or separately or with the lapse of time. A gas containing molecular oxygen is blown into the reactor, and while maintaining a predetermined pressure and temperature, the reaction is carried out for a sufficient period of time until the desired 2,6-NDA is obtained.

As the reaction proceeds, molecular oxygen is absorbed to generate a large amount of the heat of reaction. Usually, therefore, external warming or heating during the oxidation reaction is unnecessary. Rather, it is preferred to remove the heat and maintain the predetermined reaction temperature.

The removal of heat can be easily effected by known methods, for example by an internal heat removing method wherein the reaction medium such as acetic acid or water is evaporated or the blown gas is released to entrain the heat, or by an external method in which the reaction system is cooled by externally applying a cooling medium such as water or steam, or by using both of these methods.

When the starting material in the reaction system disappears and the end of the reaction draws near, absorption of molecular oxygen almost ceases apparently. The reaction is terminated at this point.

The separation and recovery of 2,6-NDA from the reaction mixture after the reaction, the purification of the recovered 2,6-NDA, the after-treatment, recycling and re-use of the mother liquor left after separation of 2,6NDA may be carried out by customary procedures used in the production of 2,6-NDA from other starting materials such as 2,6-dimethylnaphthalene or in the production of terephthalic acid from p-xylene.

When the reaction has been terminated, the presence of a reaction intermediate not completely converted to 2,6-NDA may sometimes be seen to be present in the reaction mixture. In such a case, the reaction mixture is further contacted with molecular oxygen (post-oxidation) to complete the reaction. Consequently, the yield of 2,6-NDA can be increased, and at the same time, the unwanted by-products or their intermediates are oxidatively decomposed to increase the purity of the resulting 2,6-NDA.

The post-oxidation can be carried out in the oxidation reaction vessel in which the main oxidation reaction has been carried out. Alternatively, after the main oxidation reaction, the reaction mixture is first transferred to a separate vessel, and then it is contacted with molecular oxygen for a required period of time. The reaction pressure and temperature of post-oxidation need not to be the same as those of the main reaction, and may be higher or lower.

The after-treatment of the reaction mixture obtained by post-oxidation, for example the separation and recovery of 2,6-NDA, may be carried out in the same way as described above.

The process of this invention may be carried out batchwise, semi-continuously or continuously.

Advantageously, the process of this invention is carried out continuously or semicontinuously becasue the concentration of the starting material in the oxidation reaction can be easily maintained low.

Hence, according to a preferred embodiment of this invention, there is provided a process for producing 2,6-NDA which comprises oxidizing 2,6-DIPN or its oxidation derivative as a starting material with molecular oxygen in a reaction medium containing at least 70% by weight of an aliphatic monocarboxylic acid selected from acetic acid, propionic acid and a mixture of these in the presence of an oxidation catalyst comprising (A) at least one heavy metal element selected from the group consisting of cobalt and manganese and (b) a bromine element and in the co-presence of 1.1 to 15 gram-atoms, per gram-atom of the bromine element, of an alkali metal, wherein 2,6-DIPN and/or its oxidation derivative is continuously or semicontinuously added to the reaction system, the reaction mixture containing the resulting 2,6-NDA is partly or wholly withdrawn from the reaction system, 2,6-NDA is separated from the reaction mixture, and the mother liquor is recycled to the oxidation reaction either as such or after, as required, water is removed therefrom.

The starting 2,6-DIPN or its oxidation derivative can be added to the reaction system continuously or semicontinuously (in several portions with the lapse of time). Withdrawal of part of the reaction mixture may be effected continuously or semicontinuously. The withdrawal of the whole reaction mixture may be carried out at a time.

The oxidation catalyst may be caused to be present in advance in a required amount in the reaction system, or may be added to it continuously or semicontinuously during the reaction.

The reaction mixture withdrawn from the reaction system may be subjected, as required, to the post-oxidation described above, and 2,6-NDA is separated. The whole or part of the mother liquor, either as such or after optionally removing water therefrom, can be again used in the oxidation reaction.

According to the process of this invention, 2,6-NDA obtained heretofore only in a low yield from 2,6DIPN or its oxidation derivative can be obtained easily in a high purity and yield. The process of this invention can provide 2,6-NDA of high quality at lower costs than any prior process can.

2,6-NDA obtained by the process of this invention is used, for example, as a raw material for polyesters and polyamides and gives polymers of high quality.

The following examples illustrate the process of this invention. All parts in these examples are by weight.

EXAMPLE 1

A titanium-lined pressure reaction vessel equipped with a reflux condenser, a gas blowing tube, a discharge pipe, a material feed pump and a stirrer was charged with 150 parts of glacial acetic acid (HOAc), 6.227 parts (0.01667 mole/100 g of HOAc) of cobalt acetate tetrahydrate, 6.127 parts (0.01667 mole/100 g of HOAc) of manganese acetate tetrahydrate, 2.975 parts of potassium bromide and 7.361 parts of potassium acetate, and with vigorous stirring at 200° C. and 30 kg/cm$^2$-G, 53.08 parts of 2,6-diisopropylnaphthalene (2,6-DIPN) was continuously introduced over 4 hours and an excessive amount of compressed air was passed through the reaction vessel to oxidize 2,6-DIPN.

After the end of feeding 2,6-DIPN, the reaction mixture was maintained at 200° C. and 30 kg/cm$^2$-G, and the air was continuously passed through the reaction vessel for 1 hour. The reaction product was withdrawn and a solid precipitate composed mainly of 2,6-naphthalenedicarboxylic acid (2,6-NDA) was separated. The precipitate was washed and dried to give 45.55 parts of 2,6-NDA. The yield of the product based on 2,6-DIPN was 85.08 mole%.

EXAMPLES 2 to 20 AND COMPARATIVE EXAMPLES 1-3

In each run, the same reaction vessel as used in Example 1 was charged with 150 parts of glacial acetic acid (HOAc), 6.227 parts (0.01667 mole/100 g of HOAc) of cobalt acetate tetrahydrate, 6.127 parts (0.01667 mole/100 g of HOAc) of manganese acetate tetrahydrate, and the amounts indicated in Table 1 of potassium bromide and potassium acetate, and with vigorous stirring at 200° and 30 kg/cm$^2$-G, 53.08 parts of 2,6-DIPN was fed into the reaction vessel continuously over 4 hours and at the same time, an excessive amount of compressed air was passed through it to oxidize 2,6-DIPN. After the feeding of 2,6-DIPN, the reaction mixture was maintained at 200° C. and 30 kg/cm$^2$-G, and air as continuously passed for 1 hour to complete the reaction. The reaction product was worked up in the same way as in Example 1. The yield of 2,6-NDA is shown in Table 1.

In Table 1, the amounts of KBR and DOAc and the yield of the product are actually measured values, and Br$^-$/HOAc, CO+Mn/Br, $\Sigma$K$^+$/HOAc, and $\Sigma$K$^+$/Br$^-$ are calculated from the actualy measured values.

TABLE 1

| Run No. (**) | KBr Amount (parts) | Br$^-$/HOAc (g · atom/100 g · HOAc) | Co + Mn/Br (atomic ratio) | KOAc (*) Amount (parts) | $\Sigma$K$^+$/HOAc (g · atom/100 g · HOAc) | $\Sigma$K$^+$/Br$^-$ (atomic ratio) | Yield of 2,6-NDA produced (mole %) |
|---|---|---|---|---|---|---|---|
| C. 1 | 0.298 | 0.00167 | 1/0.05 | 9.569 | 0.06667 | 40 | 71.43 |
| E. 2 | 1.488 | 0.00834 | 1/0.25 | 3.680 | 0.03333 | 4 | 83.37 |
| E. 3 | " | " | " | 8.587 | 0.06667 | 8 | 81.08 |
| E. 4 | 2.380 | 0.01333 | 1/0.4 | 5.889 | 0.05333 | 4 | 83.83 |
| E. 5 | " | " | " | 7.851 | 0.06667 | 5 | 84.82 |
| C. 2 | 2.975 | 0.01667 | 1/0.5 | 0 | 0.01667 | 1 | 63.28 |
| E. 6 | " | " | " | 2.454 | 0.03333 | 2 | 83.65 |
| E. 1 | " | " | " | 7.361 | 0.06667 | 4 | 85.08 |
| E. 7 | " | " | " | 17.175 | 0.13333 | 8 | 81.35 |
| E. 8 | 4.463 | 0.02500 | 1/0.75 | 6.134 | 0.06667 | 2.667 | 88.28 |
| E. 9 | 5.950 | 0.03333 | 1/1 | 4.907 | 0.06667 | 2 | 84.90 |
| E. 10 | " | " | " | 24.536 | 0.20000 | 6 | 82.79 |
| E. 11 | 8.925 | 0.05000 | 1/1.5 | 2.454 | 0.06667 | 1.333 | 87.54 |
| E. 12 | " | " | " | 7.361 | 0.10000 | 2 | 88.78 |

TABLE 1-continued

| Run No. (**) | KBr Amount (parts) | KBr Br⁻/HOAc (g·atom/100 g·HOAc) | Co + Mn/Br (atomic ratio) | KOAc (*) Amount (parts) | KOAc ΣK⁺/HOAc (g·atom/100 g·HOAc) | ΣK⁺/Br⁻ (atomic ratio) | Yield of 2,6-NDA produced (mole %) |
|---|---|---|---|---|---|---|---|
| C. 4 | CoBr₂, MnBr₂ | 0.0667 | 1/2 | 0 | 0 | 0 | 13.56 |
| C. 5 | MnBr₂, KBr | " | " | 0 | 0.03333 | 0.5 | 49.72 |
| E. 13 | 11.900 | 0.06667 | " | 0.981 | 0.07333 | 1.1 | 80.88 |
| E. 14 | " | " | " | 9.814 | 0.13333 | 2 | 90.71 |
| E. 15 | " | " | " | 19.629 | 0.20000 | 3 | 88.16 |
| E. 16 | " | " | " | 29.442 | 0.26667 | 4 | 82.46 |
| E. 17 | 17.850 | 0.10000 | 1/3 | 4.907 | 0.13333 | 1.333 | 85.92 |
| E. 18 | " | " | " | 14.721 | 0.20000 | 2 | 90.65 |
| E. 19 | 23.800 | 0.13333 | 1/4 | 9.814 | 0.20000 | 1.5 | 87.12 |
| E. 20 | " | " | " | 19.629 | 0.26667 | 2 | 89.70 |
| C. 3 | 29.751 | 0.16667 | 1/5 | 0 | 0.16667 | 1 | 64.70 |

(*): ΣK⁺ is the total K⁺ calculated from KBr and KOAc added to the reaction system.
(**): E = Example, C = Comparative Example As is clearly seen from the results shown in Table 1, the yield of 2,6-NDA is highest at a ΣK/Br⁻ atomic ratio of about 2/1. This ratio tends to be higher as the concentration of bromine is lower. Accordingly, it is seen that the alkali metal/bromine atomic ratios specified in the present specification and claims are best in practical applications.

The mole ratio of the heavy metals (Co, Mn) to the starting 2,6-DIPN was 0.20. In the present invention, the desired 2,6-NDA can be obtained in a yield of 90% or more by properly selecting the atomic ratio of the alkali metal to bromine. In the process disclosed in EP-A-No. 142719 cited hereinabove, similar yields can be obtained only when a very large amount of heavy metal catalyst is used relative to the starting material as shown by the Co+Mn/2,6DIPN mole ratio of from 1 to 4 (see Examples 3 to 5 and 14 of EP-A-No. 142719).

A comparison of these results readily shows that the process of this invention can produce the same result as the prior art by using a much smaller amount of heavy metal catalysts, and therefore has very practical utility. This effect is more clearly shown by using propionic acid as the solvent instead of acetic acid.

COMPARATIVE EXAMPLE 4

Example 1 was repeated except that 8.17 parts (0.0167 mole/100 g of HOAc) of cobalt bromide hexahydrate and 7.17 parts (0.0167 mole/100 g of HOAc) of manganese bromide tetrahydrate were used instead of cobalt acetate tetrahydrate and manganese acetate tetrahydrate and potassium acetate was not used. The results are shown in Table 1.

COMPARATIVE EXAMPLE 5

Example 1 was repeated except that 7.17 parts (0.0167 mole/100 g of HOAc) of manganese bromide tetrahydrate was used instead of manganese acetate tetrahydrate, the amount of potassium bromide was changed to 5.950 parts (0.03333 mole/100 g of HOAc), and potassium acetate was not used. The results are shown in Table 1.

EXAMPLE 21

The procedure of Examples 2 to 20 was repeated except that 10.289 parts (0.06667 mole/100 g of HOAc) of sodium bromide and 8.203 parts (0.06667 mole/100 g of HOAc) of sodium acetate were used instead of potassium bromide and potassium acetate. As a result, 44.68 parts of 2,6-NDA was obtained in a yield of 82.61 mole% based on 2,6-DIPN.

COMPARATIVE EXAMPLE 6

Example 4 was repeated except that 8.81 parts (0.0333 mole/100 g of HOAc) of calcium acetate monohydrate was further added to the reaction system. The resulting solid was deep brown and contained a large amount of tarry product. On drying, its weight was 33.62 parts. Analysis showed that the product contained 52.14% by weight (corresponding to 17.53 parts) of 2,6-NDA, and the yield of 2,6-NDA was 32.75 mole%.

EXAMPLE 22

The procedure of Examples 2 to 20 was repeated except that 10.486 parts (0.06667 mole/100 g of HOAc) of lithium bromide monohydrate and 6.599 parts (0.06667 mole/100 g of HOAc) of lithium acetate were used instead of potassium bromide and potassium acetate. There was obtained 40.63 parts of 2,6-NDA in a yield of 75.18 mole% based on 2,6-DIPN.

COMPARATIVE EXAMPLE 7

The procedure of Examples 2 to 20 was repeated except that 9.794 parts (0.06667 mole/100 g of ammonium bromide and 7.708 parts (0.06667 mole/100 g of HOAC) of ammonium acetate were used instead of potassium bromide and potassium acetatee. The resulting 2,6-NDA was a brown solid, and weighed 42.95 parts on drying. On analysis, its purity was low, and the yield of 2,6-NDA was only 54.22 mole%.

EXAMPLES 23-27 AND COMPARATIVE EXAMPLES 8-9

In each run, the same reaction vessel as used in Example 1 was charged with 150 parts of glacial acetic acid (HOAc), 3.114 parts (0.00833 mole/100 g of HOAc) of cobalt acetate tetrahydrate, 3.064 parts (0.00833 mole/100 g of HOAc) of manganese acetate tetrahydrate, and the amounts indicated in Table 2 of potassium bromide and potassium acetate, and with vigorous stirring at 200° C. and 30 kg/cm²-G, 53.08 parts of 2,6-DIPN was fed into the reaction vessel continuously over 4 hours and at the same time, an excessive amount of compressed air was passed through it to oxidize 2,6-DIPN. After the feeding of 2.6-DIPN, the reaction mixture was maintained at 200° C. and 30 kg/cm²-G. and air as continuously passed for 1 hour to complete the reaction. The reaction product was worked up in the same way as in Example 1. The yield of 2,6-NDA is shown in Table 2.

EXAMPLES 28-30

In each run, the same reaction vessel as used in Example 1 was charged with 150 parts of glacial acetic acid (HOAc), 12.454 parts (0.03333 mole/100 g of HOAc) of cobalt acetate tetrahydrate, 12.254 parts (0.03333 mole/100 g of HOAc) of manganese acetate tetrahydrate, and the amounts indicated in Table 2 of potassium bromide and potassium acetate, and with vigorous stirring at 200° C. and 30 kg/cm$^2$-G, 53.08 parts of 2,6-DIPN was fed into the reaction vessel continuously over 4 hours and at the same time, an excessive amount of compressed air was passed through it to oxidize 2,6-DIPN. After the feeding of 2.6-DIPN, the reaction mixture was maintained at 200° C. and 30 kg/cm$^2$-G, and air as continuously passed for 1 hour to complete the reaction. The reaction product was worked up in the same way as in Example 1. The yield of 2,6-NDA is shown in Table 2.

TABLE 2

| Run No. | KBr Amount (parts) | KBr Br$^-$/HOAc (g·atom/100 g·HOAc) | Co + Mn/Br (atomic ratio) | KOAc Amount (parts) | KOAc ΣK$^+$/HOAc (g·atom/100 g·HOAc) | ΣK$^+$/Br$^-$ (atomic ratio) | Yield of 2,6-NDA produced (mole %) |
|---|---|---|---|---|---|---|---|
| E. 23 | 2.975 | 0.01667 | 1/1 | 7.361 | 0.06667 | 4 | 74.49 |
| C. 8  | 5.950 | 0.03333 | 1/2 | 0     | 0.03333 | 1 | 71.35 |
| E. 24 | "     | "       | "   | 4.907 | 0.06667 | 2 | 83.94 |
| E. 25 | "     | "       | "   | 9.814 | 0.10000 | 3 | 81.60 |
| E. 26 | "     | "       | "   | 14.721| 0.13333 | 4 | 78.44 |
| C. 9  | 11.900| 0.06667 | 1/4 | 0     | 0.06667 | 1 | 64.55 |
| E. 27 | "     | "       | "   | 9.814 | 0.13333 | 2 | 78.85 |
| E. 28 | 5.950 | 0.03333 | 1/0.5 | 4.907 | 0.06667 | 2 | 92.23 |
| E. 29 | "     | "       | "   | 14.721| 0.13333 | 4 | 90.29 |
| E. 30 | 11.900| 0.06667 | 1/1 | 9.814 | "       | 2 | 91.63 |

EXAMPLE 31

In each run, the same reaction vessel as used in Example 1 was charged with 150 parts of propionic acid (HOPrn), 3.114 parts (0.00833 mole/100 g of DHOPrn) of cobalt acetate tetrahydrate, 3.064 parts (0.00833 mole/100 g of HOPrn) of manganese acetate tetrahydrate, 11.900 parts (0.06667 gram-atom of Br$^-$/100 g of HOPrn) of potassium bromide and 9.814 parts (0.13333 gram-atom of K$^+$/1090 g of HOPrn) of potassium acetate (therefore Co+MN/Br=1/4; ΣK$^+$/Br$^-$=2)), and with vigorous stirring at 200° C. and 30 kg/cm$^2$-G, 53.08 parts of 2,6-DIPN was fed into the reaction vessel continuously over 4 hours and at the same time, an excessive amount of compressed air was passed through it to oxidize 2,6-DIPN. After the feeding of 2,6-DIPN, the reaction mixture was maintained at 200° C. and 30 kg/cm$^2$-G, and air as continuously passed for 1 hour to complete the reaction. The reaction product was taken out, and a solid precipitate composed mainly of 2,6-NDA was separated. The separated precipitate was washed with hot acetic acid and hot water and dried to give 49.13 parts of a yellowish white microcrystalline product having a 2,6-NDA purity of 99.88%. The yield of 2,6-NDA corresponded to 90.80 mole% based on the starting 2,6-DIPN used.

When the same reaction as above was carried out using 150 parts of acetic acid instead of propionic acid (see Example 27). There was obtained 43.30 parts of a yellowish brown solid having a 2,6-NDA purity of 98.41%. The yield of 2,6-NDA corresponded to 78.85 mole% of the starting 2,6-DIPN used.

The results obtained above demonstrate that propionic acid as a reaction solvent is used prior to acetic acid in any of the yield, purity and coloration of the resulting 2,6-NDA in the presence of the same amount of the same heavy metals as catalyst. A comparison of the results of the present Example with those of Example 14 shows that in the case of using propionic acid as the solvent, the amount of heavy metals required to obtain the same yield of 2,6-NDA is one-half of that required in the case of using acetic acid solvent.

EXAMPLE 32

Example 31 was repeated except that 1.557 parts (0.00417 mole/100 g of HOPrn) of cobalt acetate tetrahydrate and 1.532 parts (0.00417 mole/100 g of HOPrn) of manganese acetate tetrahydrate (therefore, Co+Mn/Br=⅛) were used instead of the heavy metal compounds used in Example 31. There was obtained 44.01 parts of a pale ochre solid having a 2,6-NDA purity of 99.01%. The yield of 2,6-NDA corresponded to 80.63 mole% based on the starting 2,6-DIPN.

EXAMPLE 33

Example 31 was repeated except that 12.454 parts (0.03333 mole/100 g of HOPrn) of cobalt acetate tetrahydrate and 12.254 parts (0.03333 mole/100 g of HOPrn) of manganese acetate tetrahydrate (therefore, Co+Mn/Br=1/1) were used instead of the heavy metal compounds used in Example 31. There was obtained 50.20 parts of a yellowish white microcrystalline product composed of nearly pure 2,6-NDA. The yield of 2,6-NDA corresponded to 92.88 mole% based on the starting 2,6-DIPN.

EXAMPLES 34-35

Example 31 was repeated except that the reaction temperature was changed to 180° C. in Example 34° and 220° C. in Example 35. The yields of 2,6-NDA are shown in Table 3.

TABLE 3

| Example | Reaction temperature (°C.) | Yield of 2,6-NDA (mole %) |
|---|---|---|
| 34 | 180 | 88.51 |
| 31 | 200 | 90.80 |
| 35 | 220 | 85.18 |

EXAMPLES 36-38

Example 31 was repeated except that a mixture of acetic acid (HOAc) and propionic acid (HOPrn) in the amounts shown in Table 4 was used instead of 150 parts of propionic acid. The results are shown in Table 4.

TABLE 4

| Example | Amount of solvent (parts) | | | Yield of 2,6-NDA (mole %) |
|---|---|---|---|---|
| | HOAC | HOPrn | HOAc/HOPrn | |
| 27 | 150 | 0 | 100/0 | 78.85 |
| 36 | 125 | 25 | 83/17 | 83.94 |
| 37 | 100 | 50 | 67/33 | 89.15 |
| 38 | 75 | 75 | 50/50 | 91.60 |
| 31 | 0 | 150 | 0/100 | 90.80 |

The results given in Table 4 show that the effect of increasing 2,6-NDA by using only propionic acid as a reaction solvent is substantially retained even when about two-thrids of propionic acid is replaced by acetic acid which is used with preference in the prior art in such an oxidation eaction.

EXAMPLES 39-44

Example 9 was repeated except that the amounts of cobalt acetate tetrahydrate and manganese acetate tetrahydrate and the reaction temperature were changed as indicated in Table 5.

TABLE 5

| Example | Co(OAc)$_2$.4H2O | | Mn(OAc)$_2$.4H2O | | Co/Mn (atomic ratio) | Reaction temperature (°C.) | Yield of 2,6-NDA produced (mole %) |
|---|---|---|---|---|---|---|---|
| | Amount (parts) | Co/HOAc (g · atom/ 100 g) | Amount (parts) | Mn/HOAc (g · atom/ 100 g) | | | |
| 9 | 6.227 | 0.01667 | 6.127 | 0.01667 | 50/50 | 200 | 84.90 |
| 39 | 3.114 | 0.00833 | 9.191 | 0.02500 | 25/75 | " | 89.15 |
| 40 | 1.245 | 0.00333 | 11.029 | 0.03000 | 10/90 | " | 85.54 |
| 41 | " | " | " | " | " | 220 | 87.29 |
| 42 | 0.249 | 0.00067 | 12.009 | 0.03267 | 2/98 | " | 83.36 |
| 43 | " | " | 24.264 | 0.06600 | 1/99 | 200 | 87.14 |
| 44 | 0 | 0 | 12.254 | 0.03333 | 0/100 | 220 | 84.90 |

Co + Mn/Br =
1/0.5 (Example 43)
1/1 (other Examples)
$\Sigma K^+/Br^- = 2$

What is claimed is:

1. A process for producing 2,6-naphthalenedicarboxylic acid which comprises oxidizing 2,6-diisopropylnaphalene or its oxidation derivative with molecular oxygen in a reaction medium containing at least 70% by weight of an aliphatic monocarboxylic acid selected from the group consisting of acetic acid, propionic acid and a mixture of these in the presence of an oxidation catalyst comprising (A) at least one compound of a heavy metal selected from propionic acid and a mixture of these in the presence of an oxidation catalyst comprising (A) at least one compound of a heavy metal selected from the group consisting of compounds of cobalt, compounds of manganese, and mixtures thereof and (B) bromine or a bromine compound; characterized in that said oxidation is carried out in the presence of 1.1 to 15 gram-atoms, per gram-atom of bromine, of an alkali metal.

2. The process of claim 1 wherein the oxidation reaction is carried out in the presence of 1.3 to 8 -gram-atoms, per gram-atom of bromine, of the alkali metal.

3. The process of claim 2 wherein the oxidation reaction is carried out in the presence of 1.5 to 6 -gram-atoms, per gram-atom of bromine, of the alkali metal.

4. The process of claim 1 wherein the alkali metal is potassium, sodium, or lithium.

5. The process of claim 4 wherein the alkali metal is potassium or sodium.

6. The process of claim 1 wherein the amount of the alkali metal is not more than 0.4 gram-atom per 100 g of the aliphatic monocarboxylic acid.

7. The process of claim 6 wherein the amount of the alkali metal is not more than 0.25 gram-atom per 100 g of the aliphatic monocarboxylic acid.

8. The process of claim 1 wherein the aliphatic monocarboxylic acid is composed of 0 to 75% by weight of acetic acid and 100 to 25% by weight of propionic acid.

9. The process of claim 1 wherein the atomic ratio of the heavy metal elements to bromine in the oxidation catalyst is from 1:0.1 to 1:20.

10. The process of claim 1 wherein the oxidation reaction is carried out in the presence of $3.5 \times 10^{-3}$ 0.1 gram-atom, per 100 g of the aliphatic monocarboxylic acid, of the heavy metal.

11. The process of claim 1 wherein the oxidation is carried out at a temperature of 160° to 230° C.

12. The process of claim 1 wherein the oxidation is carried out under a partial oxygen pressure of 0.1 to 8 kg/cm$^2$-abs/.

13. The process of claim 1 wherein a combination of cobalt and manganese is used as the heavy metal.

14. The process of claim 13 wherein the atomic ratio of cobalt to manganese is from 5:95 to 60:40.

15. The process of claim 5 wherein the oxidation reaction is carried out in the presence of about 2 gram-atoms, per gram-atom of the bromine element, of the alkali metal.

16. The process of claim 15 wherein the alkali metal is potassium.

17. The process of claim 8 wherein the ratio of acetic acid and propionic acid is from 20:80 to 70:30.

* * * * *

UNITED STATES PATENT AND TRADEMARK OFFICE
CERTIFICATE OF CORRECTION

PATENT NO. : 4,716,245

DATED : December 29, 1987

INVENTOR(S) : ISAO HIROSE

It is certified that error appears in the above-identified patent and that said Letters Patent is hereby corrected as shown below:

On the title page

<u>IN THE ABSTRACT</u>

Line 5, "actic" should be --acetic--.

<u>IN THE CLAIMS</u>

Column 15, line 45, claim 1, "naphalene" should be --naphthalene--.

Column 15, lines 51-54, claim 1, delete "propionic acid and a mixture of these in the presence of an oxidation catalyst comprising (A) at least one compound of a heavy metal selected from".

Column 16, lines 2 and 5, claims 2 and 3, respectively, " -gram- " should be -- gram- --.

Column 16, line 24, claim 10, "$10^{-3}0.1$" should be --$10^{-3}$ to 0.1--.

Column 16, line 46, claim 12, "$kg/cm^2$-abs/" should be --$kg/cm^2$-abs--.

Signed and Sealed this

Tenth Day of May, 1988

*Attest:*

DONALD J. QUIGG

*Attesting Officer*    *Commissioner of Patents and Trademarks*